United States Patent [19]

Aswad et al.

[11] Patent Number: 5,498,253
[45] Date of Patent: Mar. 12, 1996

[54] PORT ADAPTOR AND PROTECTOR AND CONTAINER HAVING SAME

[75] Inventors: Andrew D. Aswad, Mundelein; Dale Severs, Gurnee; Joyce Silvestri, Antioch, all of Ill.; Hugh M. Forman, Waukesha, Wis.; Lecon Woo, Libertyville, Ill.; Thomas D. Hiller, Vernon Hills, Ill.; Lisa S. Walsh, Wonder Lake, Ill.; Sandra Wade, Highland Park, Ill.; Eddie Chan, Mundelein, Ill.; Patrick Balteau, Namur, Belgium; Franco Peluso, Heverlee, Belgium; Eric Henaut, Nivelles, Belgium

[73] Assignee: Baxter International Inc., Deerfield, Ill.

[21] Appl. No.: 156,486

[22] Filed: Nov. 23, 1993

[51] Int. Cl.$^6$ .................................................. A61B 19/00
[52] U.S. Cl. .................... 604/403; 604/415; 604/905; 128/DIG. 24; 215/247; 215/DIG. 3; 220/269
[58] Field of Search ............................... 604/403, 404, 604/408, 411–415, 905; 128/760, 767, 771, 912, DIG. 24; 215/230, 247, 249, DIG. 3; 220/269, 270

[56] References Cited

U.S. PATENT DOCUMENTS

| | | | |
|---|---|---|---|
| 2,923,427 | 2/1960 | Klopfenstein | 215/230 |
| 3,278,063 | 10/1966 | Kranzhoff | 215/249 |
| 3,460,702 | 8/1969 | Andrews | 215/DIG. 3 |
| 3,604,410 | 9/1971 | Whiteacre | 604/191 |
| 3,653,528 | 4/1972 | Wimmer | 215/DIG. 3 |
| 3,974,930 | 8/1976 | Gizard et al. | 215/DIG. 3 |
| 4,133,441 | 1/1979 | Mittleman et al. | 215/247 |
| 4,150,673 | 4/1979 | Watt . | |
| 4,256,333 | 3/1981 | Jones . | |
| 4,303,067 | 12/1981 | Connolly et al. . | |
| 4,350,261 | 9/1982 | Roth | 220/270 |
| 4,573,980 | 3/1986 | Karrasch et al. . | |
| 4,616,760 | 10/1986 | Kersten et al. | 215/232 |
| 4,944,736 | 7/1990 | Holtz | 604/403 |
| 5,297,599 | 3/1994 | Bucheli | 215/247 |
| 5,382,408 | 1/1995 | Perlman | 220/269 |
| 5,385,372 | 1/1995 | Utterberg | 604/905 |
| 5,390,898 | 2/1995 | Smedley et al. | 604/905 |

FOREIGN PATENT DOCUMENTS

| | | |
|---|---|---|
| 0113597 | 7/1984 | European Pat. Off. . |
| 0288250 | 10/1988 | European Pat. Off. . |
| WO85/01270 | 3/1985 | WIPO . |
| WO86/02905 | 5/1988 | WIPO . |

*Primary Examiner*—Randall L. Green
*Assistant Examiner*—P. Zuttarelli
*Attorney, Agent, or Firm*—Thomas S. Borecki; Charles R. Mattenson; Robert M. Barrett

[57] ABSTRACT

An improved adaptor and protector for same which is removably sealing an opening of the adaptor located at an end of a tubular member. The adaptor has a longitudinal passageway for receiving a cannula. An upper end of the adaptor has an interior diameter defining a first end of the passageway for receiving the cannula. A lower end of the adaptor has an interior diameter defining a second end of the passageway adapted for receiving an injection site wherein the diameter of the first end is larger than the diameter at the second end. A middle portion intermediate the first end and the second end has a tapering interior diameter for directing the cannula to the injection site and further having an exterior surface with gripping surfaces. The tapering interior diameter of the middle portion of the adaptor includes guiding members to direct the cannula or other injection devices. The adaptor may also be provided with a protector removably sealing an opening located at an end of the adaptor. The cap portion includes means extending therefrom for allowing removal of the cap portion from the adaptor. Additionally, the present invention provides an improved container assembly.

21 Claims, 2 Drawing Sheets

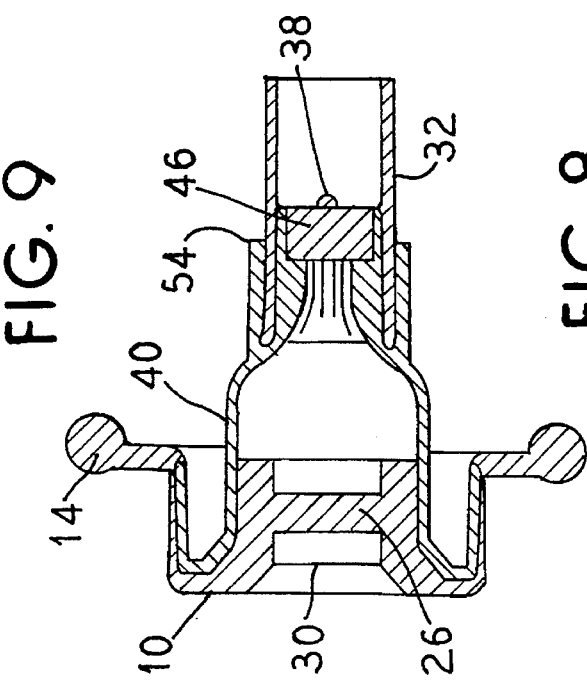
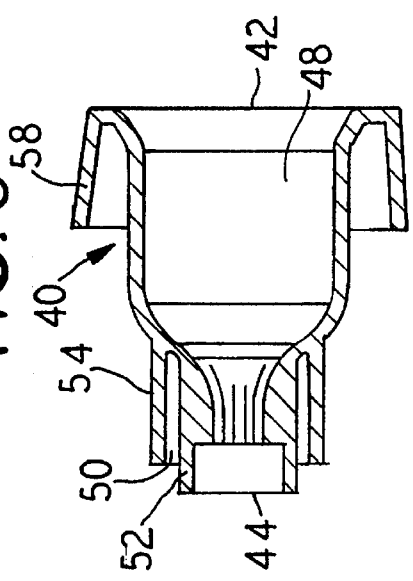
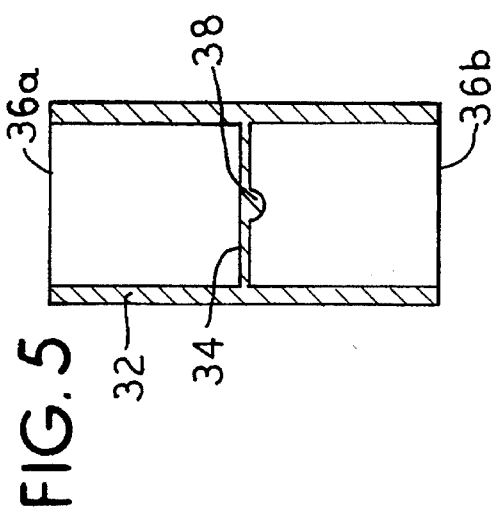
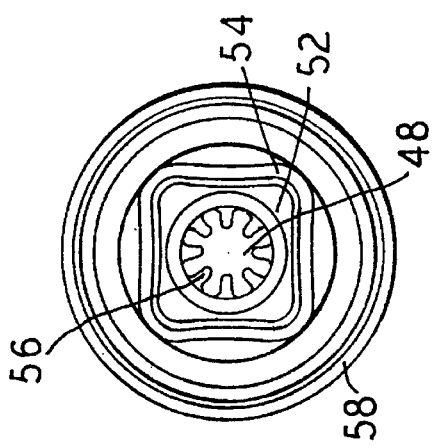
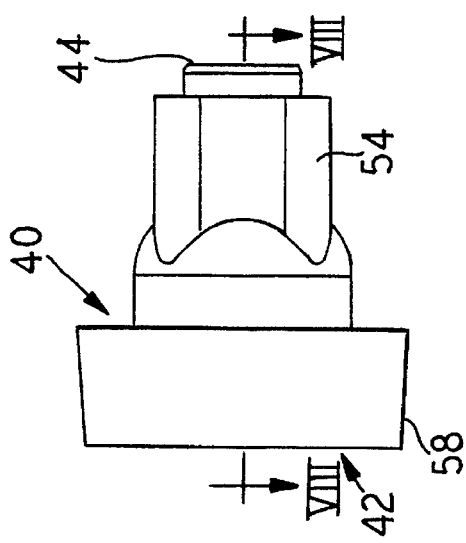

1

PORT ADAPTOR AND PROTECTOR AND CONTAINER HAVING SAME

BACKGROUND OF THE INVENTION

The present invention relates generally to containers for housing medical solutions and means for accessing same. More specifically, the present invention relates to adapters for receiving a cannula and maintaining same within a sterile environment and protectors for maintaining a sterile environment.

Housing medical solutions and products in flexible plastic containers is, of course, known. These containers provide a means for housing the solution prior to the solution being administered to a patient or used for other therapeutic applications.

Likewise, it is known to house a variety of solutions in such containers for a variety of medical procedures. Such solutions include intravenous, enteral, and peritoneal solutions. In this regard, flexible containers are used for peritoneal dialysis.

In peritoneal dialysis, a dialysis solution is introduced into a patient's peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base, electrolyte and fluid balance to be returned to the blood. The dialysis solution is simply drained from the body cavity through the catheter.

In order to access the interior of a container, either to infuse solution therein or access a solution contained therein, it is known to provide containers with one or more ports or fitments. These ports are typically tubular in shape and define a flow path from an interior of the container to the outside environment.

Such ports may include a pierceable membrane or injection site. In use, fluid is either added to the container or accessed therefrom by inserting a needle, cannula, or other member through the port piercing a membrane or an injection site.

To prevent contamination of the solution, and infection to the patient, the transfer of solution out of the container, and in many instances into the container, must take place under sterile conditions. Therefore, the distal ends of the port or connector (e.g., cannula, luer connector, etc.) are frequently capped with a "port protector." The function of the port protector is to preserve the sterile integrity of the interior of the port or connector after the entire container assembly has been assembled and terminally sterilized. Most frequently, sterilization in the medical industry is through the use of steam sterilization. Steam sterilization typically takes place under elevated temperatures and pressures, such as, for example, 120° C. (250° F.).

Currently, one method used to provide the necessary requirements of a port protector is to use a plastic sleeve, typically constructed from extruded flexible polyvinyl chloride, that is sealed off at one end with a slit opening cut along the longitudinal direction of the sleeve. During assembly, the sleeve is spread open at the slit and slipped onto the tube through the pre-slit opening. The sealed end is placed against the opening of the tube to provide the protective function. During steam sterilization, steam can penetrate through the sleeve so that a sufficient microbial kill is achieved. During use, ideally, the user or patient grabs the slit end of the sleeve and pulls it away from the tube to expose the tube for use.

Although these pre-slit sleeves have been in use for many years, a number of issues with respect to the use of same exist. For example, frequently, the sleeve develops a strong tack with the tube during steam sterilization. This can make it very difficult to remove.

Additionally, the thin walled slit part of the sleeve often becomes severely distorted during steam sterilization. This can make it extremely difficult for a patient with visual or manual impairment to remove the sleeve.

Still further, the dimensions of the flexible sleeve are difficult to control. Accordingly, relaxations of the material may occur during the steam sterilization process, causing the sleeve to come off at a later time, thereby breaching the sterile barrier.

Furthermore, during the extrusion manufacturing of the sleeve, die lines are frequently introduced in the longitudinal direction. This can reduce the sterile barrier, or at times, render the microbial barrier ineffective.

Additionally, sometimes in systems with closed ends, pressure differentials are created during sterilization. These pressure differentials can blow off the sleeve, destroying the sterile barrier.

One approach that has been used in an attempt to overcome the disadvantages of the sleeve is to use an injection molded cap to ensure the sterility of the surfaces under the protector cap. An example of such a cap is set forth in U.S. Pat. No. 4,573,980.

Injection sites which allow for the introduction of intraperitoneally administered drugs into a solution bag including the admixture of non-shelf stable nutrients and reconstituted medications are known. Prior injection sites, however, often are positioned at a distance from the solution bag requiring squeezing of the port tube to mix the drug.

Often, injection sites are small in cross-sectional areas such that a needle, cannula or other injection device, may not properly penetrate the injection site. As a result, accidental needle sticks of a user or misplaced injections through the injection site and/or other membrane often takes place. In addition, accidental puncturing of a wall of the solution bag often results.

A need, therefore, exists for an improved medication port, adaptor and protector for a container assembly, such as a solution bag used in peritoneal dialysis.

SUMMARY OF THE INVENTION

The present invention provides an improved adaptor for receiving a cannula, a needle or other injection device for connection to a tubular member defining a port of a container. The adaptor may further be covered by a protector which may be removably sealed to same. The adaptor eliminates the potential of the needle, for example, to stab or pierce either the finger of an individual or the container.

To this end, the present invention provides an adaptor, having a longitudinal passageway for receiving a cannula, located at an end of a tubular member defining a port of a container. The adaptor comprises an upper end having an interior diameter defining a first end of the passageway for receiving the cannula. The adaptor further comprises a lower end having an interior diameter defining a second end of the passageway adapted for receiving an injection site wherein the diameter at the first end is larger than the diameter at the second end. A middle portion intermediate the first end and the second end has a tapering interior diameter for directing the cannula to the injection site and further having an exterior surface with gripping surfaces.

In an embodiment of the adaptor, the tapering interior diameter of the middle portion includes guide members about the interior diameter.

In an embodiment, the exterior surface of the middle portion of the adaptor has a substantially square cross-sectional area.

In an embodiment, the upper end includes a finger guard.

In an embodiment, the lower end includes an exterior surface for securing the tubular member of the container.

In an embodiment, at least a portion of the adaptor is color coded to provide visual means for identifying product.

In an embodiment, the present invention provides an adaptor and a protector in combination, the adaptor for receiving a cannula and connecting to a tubular member of a container. The protector comprises a cap member including a top and side walls and defining an interior having a plug member engaging with an open end of the adaptor and removably sealing the open end of the adaptor, the cap portion further including means extending from the cap portion for allowing removal of the cap portion from the adaptor. The adaptor comprises a longitudinal interior passageway including an open end for removably sealing the protector, an opposite end having an interior diameter for receiving an injection site, and an exterior diameter for securing the tubular member wherein a middle portion between the open end and the opposite end includes a tapering interior diameter for directing the cannula to the injection site.

In an embodiment, the adaptor of the combination includes a guard at the open end having a diameter larger than the middle portion.

In an embodiment, the adaptor of the combination includes guiding members in the middle portion about the interior diameter.

In an embodiment, the middle portion of the adaptor includes an exterior gripping surface.

In an embodiment, the adaptor of the combination includes a passageway which narrows from the open end to the opposite end.

In an embodiment, at least a portion of the adaptor or at least a portion of the protector of the combination is color coded to provide visual means for identifying product.

In an embodiment, the means extending from the cap portion of the protector of the combination includes a ring that extends from opposite side walls of the cap portion.

In an embodiment, the present invention provides a protector for removably sealing an opening located at an end of an adaptor. The protector comprises a cap portion including a top and side walls and defining an interior for receiving the end of the adaptor and removably sealing the opening of the adaptor. A plug member within the interior of the cap portion engages with the opening of the adaptor removably sealing the opening of the adaptor. The cap portion includes a means extending from the cap portion for allowing removal of the cap portion from the adaptor.

In an embodiment, at least the top of the cap portion is constructed from a steam permeable material.

In an embodiment, the entire protector is constructed from the same material.

In an embodiment, the present invention provides a container assembly comprising: a container having an interior and designed to house a solution and further having at least one port. A tubular member defines a passageway providing fluid communication with the interior of the container. An adaptor defines a longitudinal passageway connected to and extending from the tubular member at a proximal end having an inner diameter for receiving an injection site and further having a distal end having an inner diameter larger than the inner diameter of the proximal end wherein the passageway tapers from the distal end to the proximal end to receive and direct a cannula to the injection site. A protector having a cap portion and side walls defining an interior removably seals the distal end of the adaptor.

In an embodiment, the injection site is press fit into the adaptor.

In an embodiment, the injection site is inserted prior to molding of the adaptor.

It is, therefore, an advantage of the present invention to provide an improved adaptor.

Still further, an advantage of the present invention is to provide an improved protector for the adaptor and container assembly having same.

Furthermore, an advantage of the present invention is to provide an adaptor with a tapered interior for receiving a cannula, needle or other injection device.

Additionally, an advantage of the present invention is to provide an adaptor with a rigid gripping surface to securely hold same.

Further, an advantage of the present invention is to provide an adaptor which prevents accidental needle sticking of the user.

Moreover, an advantage of the present invention is to provide an adaptor having a large target opening for receiving the cannula, needle or other injection device.

Another advantage of the present invention is to provide an adaptor which prevents puncturing of a container to which the adaptor is attached.

A still further advantage of the present invention is to provide an adaptor and/or port protector that can include means for visually indicating the solution contained within the container.

Further, an advantage of the present invention is to provide a protector that meets the functional requirements necessary to provide a sterile barrier to the adaptor and port of the container.

Moreover, an advantage of the present invention is to provide a protector and adaptor which can be used for a peritoneal dialysis container.

Another advantage of the present invention is that it provides a protector that is easily removed from the adaptor, even by weak or disabled patients.

Additional features and advantages of the present invention are described in, and will be apparent from, the detailed description of the presently preferred embodiments and from the drawings.

BRIEF DESCRIPTION OF THE DRAWINGS

FIG. 5 illustrates a cross-sectional view of a membrane tube for use in a port of the container of FIG. 1.

FIG. 6 illustrates a perspective view of an adaptor for connection to a port at one end and to a protector at an opposite end.

FIG. 7 illustrates a top plan view of the adaptor of FIG. 6.

FIG. 8 is a cross-sectional view of the adaptor taken generally along lines VIII—VIII of FIG. 6.

FIG. 9 illustrates a cross-sectional view of an injection site within the adaptor connected to the membrane tube and the protector of the present invention.

DETAILED DESCRIPTION OF THE PRESENTLY PREFERRED EMBODIMENTS

The present invention provides an improved adaptor connected to a port including a protector for the adaptor as well as a container having same. As used herein, "adaptor" refers to a device for connecting to a port or membrane tube on a container, and "protector" refers to a device for maintaining a sterile barrier at one end of the adaptor opposite the other end of the adaptor which connects to the port or membrane tube so as to maintain a sterile barrier at an opening of a tubular member that provides a fluid path from an interior to a second environment. Therefore, the adaptor of the present invention can be used on a wide variety of ports or tubes located on containers or remote from containers, and the protector can be used on the adaptor of the present invention, as well as the port directly or other fitments or luer connectors at the end of a fluid line.

Figure 1:
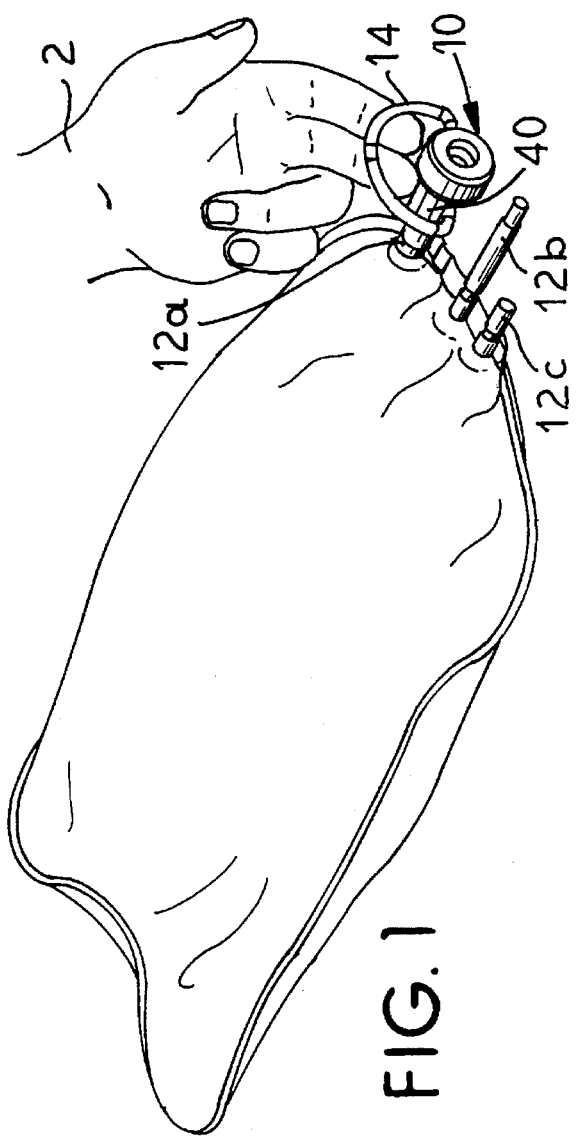
FIG. 1 illustrates a perspective view of the protector and adaptor connected to a container having a plurality of ports.

Referring now to FIG. 1, a container 1 is illustrated having a protector 10 and an adaptor 40 intermediate the protector 10 and a port 12a of the container 1. The container 1 may include other ports 12b and 12c as required for the particular application and use of the container 1. As illustrated, a user 2 can selectively remove the protector 10 from the adaptor 40 with the assistance of a pull ring 14.

Figure 4:
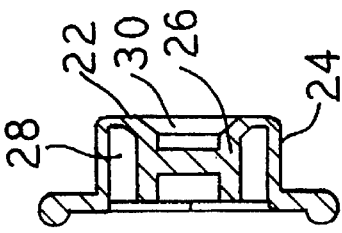
FIG. 4 illustrates a cross-sectional view of the protector of the present invention taken generally along lines IV—IV of FIG. 3.
Figure 3:
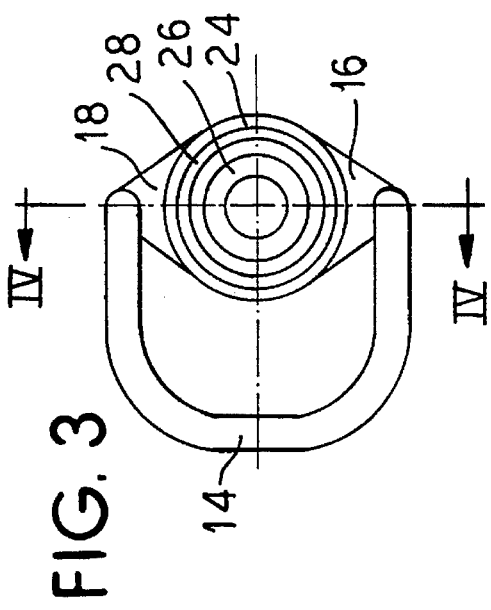
FIG. 3 illustrates a bottom plan view of the protector of the present invention.
Figure 2:
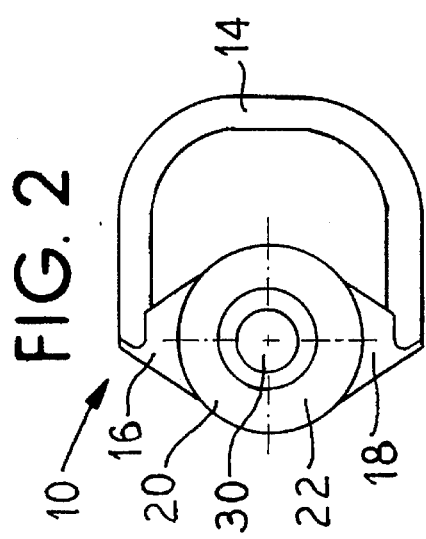
FIG. 2 illustrates a top plan view of the protector of the present invention.

Referring now to FIGS. 2–4, an embodiment of the protector 10 is illustrated. The protector 10 includes a cap 20 and the pull ring 14. The cap 20 includes legs 16 and 18 and a top 22. In an embodiment, the top 22 of the protector 10 may be sufficiently thin and of adequate composition, such as a thermoplastic elastomer, to allow steam to penetrate the top 22 and enter an interior of a connector, such as a passageway of the adaptor 40 illustrated in FIGS. 6–8 and which will be further described hereinafter. In the alternative, the protector 10 may be an injection molded polyvinyl chloride material.

When the cap 20 is constructed from a thermoplastic elastomer, the cap 20 will allow steam to penetrate the top 22 of the cap 20 and enter an interior of the adaptor 40, for example, to which the protector 10 is secured. Further details with respect to materials for the adaptor 40 are described in commonly assigned co-pending U.S. patent application entitled "Improved Port Protector and Containers Having Same", and having Ser. No. 08/075,158, herein incorporated by reference.

Preferably, the protector 10 includes the pull ring 14. The pull ring 14 extends from the legs 16 and 18 at a base of a peripheral sidewall 24. Preferably, a plane defined by the pull ring 14 is parallel to a plane defined by the top 22 of the cap 20. Therefore, a simplified mold can be used that only includes two mating halves.

The inner surface of the cap 20 includes a plug member 26. The plug member 26 ensures a good seal with the interior diameter of the adaptor 40 or the port 12a over which the protector 10 may be removably sealed. A peripheral recessed ring 28 within the interior of the protector 10 and about the plug member 26 is designed to securely mate with the exterior wall of the adaptor 40 at one end of the adaptor 40.

The pull ring 14 as illustrated in FIGS. 2–4 is a "D" shape. However, other shapes and configurations may be implemented. The top 22 of the adaptor 10 may include a recessed portion 30. The recessed portion 30 partially forms the plug member 26 within the interior of the protector 10.

If desired, means can be provided on the protector 10 for allowing a patient or other user 2 to identify the contents. This means can include color coding of at least a portion of the protector 10 so that the color will indicate the contents of the container 1. If the product is to be used by a visually impaired patient, for example, which may include a patient requiring CAPD, protrusions, which can be felt by the user 2, can be located on the pull ring 14 of the protector 10, if desired.

Due to the structure of the protector 10 and material used, the container 1 including the protector 10 can be removably sealed, for example, on any of the ports 12a, 12b and/or 12c of the container 1. In the alternative, the protector 10 can be removably sealed to the adaptor 40 extending from a fluid tube 32 and can be terminally sterilized using steam sterilization. A further sterilization step with ionizing radiation may not be required. Due to thickness and material composition of the protector 10, steam can easily penetrate the top 22 of the protector 10 sterilizing the interior of the port 12a or a connector, such as the adaptor 40.

Additionally, the protector 10 provides the necessary elastomeric properties required by such a product. In this regard, an elastomeric material is chosen that will return substantially to the original shape after having been stretched or maintains a significant retraction force long after the deformation step. In order to maximize processing efficiency, a melt processable rubber, thermoplastic elastomer, is used. The thermoplastic elastomer should provide needed processability. Additionally, the thermoplastic elastomer may be chosen to provide hydrophilicity which provides steam permeability.

Referring now to FIG. 5, a membrane tube 32 is generally illustrated which can comprise or be connected to a port, such as one of the ports 12a, 12b and 12c of FIG. 1. The membrane tube 32 is generally cylindrical having a passageway therethrough and a dividing wall 34 intermediate the open ends 36a and 36b. While the tube 32 is illustrated as a separate component of the assembly, the tube 32, of course, may be integrally formed in the container 1 or otherwise secured within the container 1 at one or more of the ports 12a, 12b and/or 12c.

Referring now to FIGS. 6–8, the adaptor 40 is generally illustrated. A first end 42 is open forming a wide mouth for receiving the needle, cannula or other injection device. An exterior wall of the open end 42 mates with the interior plug member 26 of the protector 10 when the same is secured thereto as illustrated in FIGS. 1 and 8.

The exterior of the adaptor 40 narrows from the first end 42 to the second end 44. The second end 44 has an exterior diameter which frictionally mates with the membrane tube 32 which may be inserted into the port 12a, for example, of the container 1. The interior diameter of the adaptor 40 at the second end 44 receives an injection site 46, such as a septum, and is secured therein. When the membrane tube 32 is attached to the adaptor 40, the dividing wall 34 prevents the injection site 46 from being forced through the membrane tube 32.

Referring now to FIGS. 7 and 8, a passageway 48 is formed between the first end 42 and the second end 44 of the adaptor 40. The membrane tube 32 is attached to the adaptor 40 within a clearance area 50 defined between a wall 52 extending from the second end 44 and an exterior wall 54 which may at least partially extend over the wall 52.

As illustrated in FIG. 7, the exterior wall 54 has a substantially square cross-sectional area, and the wall 52 has a substantially circular cross-sectional area. The wall 52 includes a plurality of guides 56 which direct the needle, cannula or other injection device through the injection site 46 and the dividing wall 34 of the membrane tube 32, and secure the injection site 46 within the end 44 of adaptor 40 upon removal of such injection device. The exterior walls 54 are slightly concave so as to provide gripping surfaces for the user 2 of the container 1.

The passageway 48 is defined by the first end 42 internally tapering from the end 42 for securing to the plug member 26 of the protector 10. A first portion of the passageway 48 near the first end 42 has a substantially equivalent cross-sectional area and then begins to taper at a point intermediate the first end 42 and the second end 44. The interior of the passageway 48 provides a portion through which the needle, cannula or other injection device may be inserted to a protected area to prevent piercing or puncturing of the container 1 or sticking of a finger of a user 2.

Following the insertion of the injection device into the first end 42 having a wide mouth, the passageway 48 then becomes substantially tapered as shown in FIG. 8 at a portion of the passageway 48 at which the guides 56 project equidistantly from the side walls towards the interior of the passageway 48. The guides 56 direct the needle, therefore, to pierce the injection site 46 in a desired manner, that is, preferably centrally. The needle then penetrates the injection site 46 which has been secured within the passageway 48 at the end 44 of the adaptor 40. Since the needle is forced through the injection site 46 in a desired manner, the dividing wall 34 of the membrane tube 32 will also be pierced accordingly.

Referring now to FIG. 9, the injection site 46 is shown secured within the interior diameter of the second end 44 of the adaptor 40. After the injection site 46 is secured in place, the membrane tube 32, if it is separate from the container, may be attached. In the alternative, the adaptor 40 and the injection site 46 may be attached directly to the container 1 as shown in FIG. 1 having the membrane tube 32 and/or other connector secured to one of the ports 12a as illustrated.

As illustrated in FIG. 9, the protector 10 is removably sealed to the interior passageway 48 of the adaptor 40. To protect the adaptor 40, the injection site 46 and the interior surfaces of the membrane tube 32 and the dividing wall 34 from touch contamination and other sterility issues, the protector 10 is positioned thereover. Due to the structure of the protector 10, the entire unit—the adaptor 40, the protector 10, the injection site 46 and the tube 32 along with the container 1—can be steam sterilized. Therefore, the entire system may be sterilized with the integral removable protector 10 connected to the adaptor 40.

To use, the passageway 48 of the adaptor 40 provides a funnel-like guide which may accept a variety of injection devices. Prior to inserting such an injection device, the pull ring 14 of the protector 10 may be removed by holding the exterior wall 54 of the adaptor 40 and pulling the ring 14 for removal of the protector 10 from within the adaptor 40.

In a preferred embodiment, the protector 10 includes the pull ring 14 having the configuration shown in FIG. 2. However, of course, other configurations may be implemented. In addition, alternatively, the protector 10 may be a peelable film having a tab which the user may use to peel the heat-sealed peelable film from the adaptor 40.

As previously discussed, the adaptor 40 as illustrated includes the positive-stop internal guides 56 focusing the needle or other injection device within the adaptor 40 to penetrate the injection site 46 in a desired manner. The membrane tube 32 may, therefore, be penetrated in the same predetermined manner. In addition, an exterior guard 58 of the adaptor 40 preferably encompasses the first end 42 so as to protect fingers of the user 2 of the system when initially inserting the needle into the first end 42.

The adaptor 40 is preferably made of a rigid non-PVC, non-DEHP material, such as a thermoplastic material (TPM), for example, polycarbonate. A TPM can provide rigidity for the needle inserted therein preventing puncture or piercing of same. A TPM further provides stability during use as well as promotes proper sealing between a generally softer material used for the membrane tube 32. A TPM also provides a bond between the adaptor 40 and the injection site 46 when secured in the adaptor 40. The adaptor 40, may be a single piece with the injection site 46 press fit therein or, in the alternative, the adaptor 40 may be a two-piece arrangement having a snap fit or friction weld. In this arrangement, the injection site 46 is first placed in the adaptor 40 and then the adaptor 40 is integrally formed. The adaptor 40, after inserting the injection site 46 and covering with the protector 10, may be sealed into the tube 32 as illustrated in FIG. 9.

The injection site 46 may be stamped or compression molded from either a natural rubber or a synthetic rubber. The material of the injection site 46 is dependent upon the application, such as whether resealability, for example, is required. The injection site 46 is generally disc-shaped and secured between the adaptor 40 with a pinch fit, or cut-shape and insert molded into the adaptor 40.

It should be understood that various changes and modifications to the presently preferred embodiments described herein will be apparent to those skilled in the art. Such changes and modifications can be without departing from the spirit and scope of the present invention and without diminishing its attendant advantages. It is, therefore, intended that such changes and modifications be covered by the appended claims.

I claim as my invention:

1. An adaptor securable to an end of a tubular member defining a port of a container, the adaptor comprising:

an upper end having an interior diameter defining a first end of a passageway capable of receiving a cannula;

a lower end having an interior diameter defining a second end of the passage, the lower end capable of receiving an injection site wherein the diameter at the first end is larger than the diameter at the second end;

a middle portion intermediate the first end and the second end having a tapering interior diameter, the middle portion directing the cannula to the injection site and further having an exterior surface with gripping surfaces wherein the tapering interior diameter of the middle portion includes spaced guiding members extending inwardly from an inner periphery of the tapering interior diameters of the middle portion in a substantially perpendicular direction from the inner periphery of the tapering interior diameter.

2. The adaptor of claim 1 wherein one end of the tapering interior diameter of the middle portion has a smaller diameter than the interior diameter of the lower end.

3. The adaptor of claim 1 wherein the exterior surface of the middle portion has a substantially square cross-section.

4. The adaptor of claim 1 further comprising:

a finger guard at the upper end.

5. The adaptor of claim 1 further comprising:

an exterior surface at the lower end capable of securing the tubular member of the container.

6. The adaptor of claim 1 wherein at least a portion of the adaptor is color coded to provide visual means for identifying product.

7. In combination, an adaptor including a port protector coupled thereto that is secured to a tubular member of a container, the combination comprising:

a port protector comprising a cap member portion including a top and side walls and defining an interior having a plug member capable of engaging an open end of the adaptor and removably sealing the open end of the adaptor, the cap portion further including means extending from the cap portion for allowing removal of the cap portion from the adaptor; and the adaptor comprising a longitudinal interior passageway including an open end capable of being removably sealed by the protector wherein the side walls of the port protector extend around an exterior of the open end of the adaptor and the plug member is received within the open end of the adaptor, an opposite end having an interior diameter capable of receiving an injection site and an exterior diameter capable of securing the tubular member wherein a middle portion between the open end and the opposite end includes a tapering interior diameter directing a cannula to the injection site.

8. The adaptor of claim 7 further comprising:

a guard at the open end of the adaptor having a diameter larger than the middle portion.

9. The adaptor of claim 7 further comprising:

guiding members about the interior diameter of the middle portion of the adaptor.

10. The adaptor of claim 7 wherein the passageway of the adaptor narrows from the open end to the opposite end.

11. The adaptor of claim 7 further comprising:

a ring that extends from opposite side walls of the cap member portion.

12. The adaptor of claim 7 wherein the means extending from the cap portion is a ring that extends from the side walls in a plane parallel to a plane defined by a top of the cap portion.

13. A container assembly comprising:

a container having an interior and designed to house a solution and further having at least one port;

a tubular member defining a passageway providing fluid communication with the interior of the container through the port;

an adaptor defining a longitudinal passageway between a proximal end and a distal end, the adaptor connected to and extending from the tubular member at the proximal end having an inner diameter capable of receiving an injection site wherein the distal end has an inner diameter larger than the inner diameter of the proximal end and further wherein the passageway tapers to narrow the inner diameter from the distal end to the proximal end to receive and direct a cannula to the injection site, the adaptor further having guides within the passageway of the adaptor; and a protector having a cap portion and side walls defining an interior capable of removably sealing the distal end of the adaptor.

14. The assembly of claim 13 further comprising:

means extending from the cap portion allowing removal of the cap portion from the adaptor.

15. The assembly of claim 13 further comprising:

a guard extending around a periphery of the adaptor and integrally formed with the adaptor.

16. The assembly of claim 13 further comprising:

an exterior gripping surface on the adaptor.

17. The assembly of claim 13 further comprising:

a tapering interior diameter portion intermediate the proximal end and the distal end of the adaptor.

18. The assembly of claim 13 wherein the injection site is press fit into the adaptor.

19. The assembly of claim 13 wherein the injection site is inserted prior to molding of the adaptor.

20. The assembly of claim 13 further comprising:

a plug member within the interior of the protector capable of engaging with the distal end of the adaptor and removably sealing the adaptor.

21. A container assembly comprising:

a container having an interior and designed to house a solution and further having at least one port;

a tubular member defining a passageway providing fluid communication with the interior of the container through the port;

an adaptor defining a longitudinal passageway between a proximal end and a distal end, the adaptor connected to and extending from the tubular member at the proximal end having an inner diameter capable of receiving an injection site wherein the distal end has an inner diameter larger than the inner diameter of the proximal end and further wherein the passageway tapers to narrow the inner diameter from the distal end to the proximal end to receive and direct a cannula to the injection site;

a protector having a cap portion and side walls defining an interior capable of removably sealing the distal end of the adaptor; and a plug member within the interior of the protector capable of engaging with the distal end of the adaptor and removably sealing the adaptor.

* * * * *